United States Patent [19]

Kulsrestha et al.

[11] Patent Number: 5,547,905
[45] Date of Patent: Aug. 20, 1996

[54] CATALYST AND A PROCESS FOR PREPARING CARBOXYLIC ACIDS USING THE CATALYST

[75] Inventors: Girindra N. Kulsrestha; Mahendra P. Saxena; Ashok K. Gupta; Hari B. Goyal; Rameshwar Prasad; Turuga S. R. Prasada Rao, all of Dehradun; Prakash D. Patel, Surat, all of Ind.

[73] Assignee: Council of Scientific & Industrial Research, New Delhi, Ind.

[21] Appl. No.: 280,658

[22] Filed: Jul. 27, 1994

[51] Int. Cl.⁶ .................... B01J 29/06; C07C 69/34; C07C 69/52
[52] U.S. Cl. .............. 502/66; 502/74; 560/190; 562/543; 562/595
[58] Field of Search .................... 562/543, 595; 560/190; 502/66, 74

[56] References Cited

U.S. PATENT DOCUMENTS

| | | | |
|---|---|---|---|
| 4,141,861 | 2/1979 | Courty et al. | 252/462 |
| 4,217,309 | 8/1980 | Unemura et al. | 568/477 |
| 5,041,622 | 8/1991 | LeSuer | 560/190 |

*Primary Examiner*—José G. Dees
*Assistant Examiner*—Rosalynd A. Williams
*Attorney, Agent, or Firm*—Michael D. Bednarek; Kilpatrick & Cody

[57] ABSTRACT

A catalyst comprising 70–99% by wt. of cobaltic salt and 1–30% by wt. of ferric salt, the acid component of the salt being such as acetate; propionate; naphthenate adipate and phthalate; a process for preparing the above catalyst, and a process for the preparation of carboxylic acids by oxidation of a hydrocarbon with oxygen or air in the presence of the above catalyst.

10 Claims, No Drawings

CATALYST AND A PROCESS FOR PREPARING CARBOXYLIC ACIDS USING THE CATALYST

This invention relates to a new catalyst which is useful for the preparation of carboxylic acids, a process for preparing the catalyst and its use in the production of carboxylic acids. This invention particularly relates to a catalyst which is useful for the preparation of carboxylic acids by oxidation of hydrocarbons. This invention more particularly relates to a catalyst which is highly efficient for oxidising specific hydrocarbons such as cyclopentane, cyclohexane, cycloheptane, $C_4$–$C_6$ paraffins, toluene, O-xylene, m-xylene, p-xylene and the like. The oxidation can be effected in one step in liquid phase by air or oxygen. The catalyst of the present invention is particularly useful for the preparation of dicarboxylic acids like adipic acid, pimelic acid, glutaric acid, phthalic acid etc. and mono carboxylic acids like acetic acid and benzoic acid.

Major applications of dicarboxylic acids are in the production of polyesters, polyamides, plasticizers, synthetic lubricants and alkyds. Adipic acid in particular finds wide application in the production of Nylon 66, special grade plasticizers, synthetic lubes, alkyds and polyurethanes. Monocarboxylic acids are used as solvents and in the synthesis of plasticizers and fine chemicals. Generally, dicarboxylic acids are produced by catalytic oxidation of hydrocarbons employing transition metal catalyst for example cobalt or manganese. In such processes, some times, the intermediates formed need to be separated and further subjected to oxidation depending on their reactivities with the oxidizing agents employed.

As an example, adipic acid is made by oxidizing cyclohexane to a mixture of cyclohexanone and cylohexanol in the first step followed by oxidation of this mixture by air or nitric acid to adipic acid in the second step. Currently, adipic acid is produced from cyclohexane by a two step oxidation process. In the first step cyclohexane is oxidised in a liquid phase at about 150° C. by air or oxygen in presence of a cobalt or a manganese catalyst to form a mixture of cyclohexanone and cylohexanol. In the second step this mixture is oxidized by nitric acid at 50°–80° C. in presence of a vanadium-copper catalyst to adipic acid. The overall selectivity to adipic acid is around 70% based on cyclohexane. Other processes are also known which involve either high concentrations of hydroperoxides or utilise bromide-containing catalysts or high concentrations of cobalt salts as catalysts for oxidizing cyclohexane.

The catalysts used for carrying out the above said processes have the following disadvantages:

1. Low (3–8%) conversion of cyclohexane per pass, requiring recycle of around 95% of the cyclohexane in the first step.
2. High concentration (0.2–10%) of hydroperoxides makes the process hazardous due to their explosive character at the reaction temperature employed viz. about 150° C.
3. The processes results in the formation of undesirable by-products like lactones and oxy-acids during the reaction which are required to be separated. The separation of these undesired products requires complicated steps.
4. Use of bromide catalysts leads to severe corrosion of the apparatus. Since the process operates at 5–25 kg/cm$^2$, such corrosion can also lead to explosion hazards. Further the presence of gaseous pollutants containing oxides of nitrogen from nitric acid which is used as oxidizing agent in the second step leads to severe corrosion and environmental problems.
5. Requirement of separate oxidation reactor systems for each oxidation step.

In order to raise the product selectivities, cobalt catalysts consisting of manganese, nickel, chromium, copper, or zinc salts along with cobalt salts have been used but these have not resulted in the removal of the drawbacks mentioned above.

Preparation of adipic acid by one step air oxidation of cyclohexane has been investigated earlier also. Publications of K. Tanaka in Chem. Tech. 4(9), 1974 p 555–559 in Chem Eng. News 52(15) 1974 p-24, in preprints (Div Petr Chem) Amer, Chem. Soc. 19(1), 1974 p 103–111, and Japanese Patent 75 19, 534 and of JGD Schulz and A Onopchenko in J Org. Chem. 38, 1973 p. 3729–3733 and in J Org Chem 45, 1980 p 3716–3719 and U.S. Pat. No. 4,263,453 describe such single step processes using cobalt catalysts. A recent patent by Steinmetz et al U.S. Pat. No. 4,902,827 describes the use of Zirconium and Hafnium salts in fairly large concentrations along with cobalt. A U.S. Pat. No. 3,649,689, claims the air oxidation of cyclohexane to adipic acid using a catalyst comprising of cobalt carboxylates and bromine compounds.

In these previous attempts for preparing adipic acid by oxidation of cyclohexane in one step, the main focus is on the use of cobalt catalyst and at lower oxidation temperatures ranging from 80°–130° C.

Tanaka also described the use of promoters like acetaldehyde, 2-butanone, cyclohexanone etc to convert in situ cobaltous to the catalytically active cobaltic state. These promoters are to be continuously fed to the reactor to maintain the catalyst activity.

The drawbacks of the above said hitherto known one step processes for preparing adipic acid are:

1. The adipic acid formed is of low purity as initial high proportion of cobaltous salt leads to the formation of caprolactone that polymerised quickly to polycaprolactones.
2. Use of rare metals such as hafnium, zirconium etc. as cocatalysts is expensive and monitoring of their concentration is a complicated proposition.
3. Use of bromide as cocatalyst calls for special non-corrosive material of construction of the reactor and other process equipments thereby increasing the cost of the process.

The main objective of the present invention are:

1. To provide a new catalyst which is useful for the oxidation of hydrocarbons such as cyclohexane, cyclopentane, cycloheptane, toluene, o-xylene, m-xylene and p-xylene and the like by air or oxygen to the corresponding carboxylic acids with product selectivity over 70% and higher (60–98%) hydrocarbon conversion.
2. To provide a process for the preparation of said novel catalyst from the corresponding mixtures of cobaltous and ferrous salts.
3. To provide an improved process for the production of carboxylic acids by oxidation of an appropriate hydrocarbon with air or oxygen using the novel catalyst consisting of a mixture of 70–99% by weight of cobaltic salt and 1–30% by weight of ferric salt with the high hydrocarbons conversion 60–98% and carboxylic acid selectivity over 70%. The acid component of the salt being acetate, propionate, naphthenate, adipate, phthalate or the like.
4. To provide an improved process for the preparation of dicarboxylic acids in which formation of undesired by-products such as lactones, oxy acids etc. are reduced substantially or eliminated.

Accordingly the present invention provides a novel catalyst useful for the preparation of carboxylic acids by the oxidation of hydrocarbons which comprises 70–99% by weight of cobalt salt and 1–30% by weight of ferric salt, the acid component of the salts being selected from acetate, propionate, naphthenate, adipate, phthalate and the like.

The present invention also provides a process for the preparation of the novel catalyst which is useful for the preparation of carboxylic acids by the oxidation of hydrocarbons, which comprises reacting a mixture of 70–99% by weight of the corresponding salts of cobaltous and 1–30% by weight of the corresponding salts of ferrous in the presence of an initiator, and a solvent selected from aliphatic mono-carboxylic acids having carbon atoms ranging from 2 to 4, or a mixture thereof and oxygen or air, at a temperature in the range of 60°–150° C. and pressure in the range of 1–50 kg/cm$^2$ for a period in the range of 0.25–8 hours.

The acid component of the cobaltous salt and the ferrous salt may be selected from acetate, propionate, naphthenate, benzoate, adipate, phthalate or the like. The amount of the cobaltous salt may preferably range from 85–99% by weight ferrous salt from 1–15% by weight. The initiator used may be selected from 2-butanone, paraldehyde, cyclohexanone, cyclohexanol, acetaldehyde, partly oxidized hydrocarbons and the like or their mixtures. The amount of initiator used may range from 10–100% by wt of the cobaltous salt. The solvent used may be selected from acetic acid, propionic acid, butyric acid and the like or their mixtures. The amount of initiator used may preferably range from 30–50% by weight of the cobaltous salt. The solvent used may range from 2000–12000% by weight of the cobaltous salt.

The reaction may be effected at any oxygen or air space velocity, preferably in the range of 30–60 h$^{-1}$. The temperature used may preferably in the range of 80°–130° C. The pressure employed may be preferably in the range of 1–10 kg/cm$^2$. The contacting time with air or oxygen may preferably be in the range of 0.25–3 hours.

According to another object of the present invention, there in provided an improved process for the preparation of carboxylic acids by oxidation of a hydrocarbon with oxygen or air which comprises:

(a) Containing the hydrocarbon with a catalyst comprising 70–99% by weight of cobaltic salt and 1–30% by weight of ferric salt the acid component of the salt being selecting from acetate, propionate, naphthenate, adipate, phthalate and the like.

(b) Contacting the resulting mixture with oxygen or air at a pressure in the range of 1–70 kg/Cm$^2$ and a temperature range of 60°–150° C. for a period ranging between 1 and 8 hours at a space velocity of 1–200 h$^{-1}$.

(c) Separating the unreacted hydrocarbon and the catalyst by conventional methods.

(d) Separating the carboxylic acids formed by crystallization or by fractional distillation.

(e) Recycling, if desired, the resulted hydrocarbons, solvent and the catalyst in the steps (b) to (c) above.

In a preferred embodiment of the present invention, the catalyst to hydrocarbon ratio used in the reaction ranges between 0.01 to 0.5 by weight, the pressure used ranges from 10–50 kg/cm$^2$ and the temperature used ranges from 70°–150° C. and the space velocity ranges from 1–60 h$^{-1}$.

According to the specific feature of the present invention there is provided an improved process for the preparation of adipic acid which comprises:

(a) Contacting cyclohexane with a catalyst;

(b) Contacting the resulting mixture with oxygen or air at a pressure in the range of 1–70 Kg/cm$^2$ and a temperature in the range of 70°–150° C. for a period in the range of 1–8 hrs at a space velocity of 1–200 h$^{-1}$;

(c) Separating the unreacted cyclohexane and the catalyst by conventional methods;

(d) Separating the adipic acid formed by crystallization or by fractional distillation; and (e) recycling, if desired, the unreacted cyclohexane, the solvent and the catalyst from the steps (b) to (c).

The catalyst of the present invention when tested by oxidizing hydrocarbons such as cyclohexane, cycloheptane, cyclopentane, toluene and xylenes, as explained above, it was found that the selectivity of the production of carboxylic acids ranged from 70 to 79% in cycloparaffin oxidation and 94–98% for toluene and xylenes with hydrocarbon conversions ranging between 80 and 90%. The product selectivities using the above described catalysts were found to be 2–4% higher than the maximum attainable using the hitherto known catalysts. The unreacted and partly oxidized hydrocarbons and the solvent after the separation of the acid products may be recycled to recover additional quantity of the acid, thereby increasing the efficiency of the process.

It is also to be noted that the examples given below are by way of illustrating the invention only and therefore should not be considered to limit the scope of the invention.

Examples 1–3 describe the process of preparing the novel catalyst of the present invention.

EXAMPLE I

A solution of 18 g cobaltous acetate, Co(OCOCH$_3$)$_2$.4H$_2$), 2 g ferrous acetate, 3 g cyclohexanone in 500 g acetic acid was heated to 95° C. and treated with oxygen at a space velocity of 20 h$^{-1}$ for one hour until the combined concentration of cobaltic and ferric ions was about 85% of the total metal ions. At this stage the concentration (wt % of the total metal salts) of various ions in the catalyst so prepared was found to be: cobaltic acetate 79%, cobaltous acetate 11%, ferric acetate 6%, ferrous acetate 4%.

EXAMPLE II

A solution of 17 g cobaltous naphthenate, 3 g ferrous naphthenate and 3.5 g 2-butanone in 400 g acetic acid was heated to 100° C. and treated with stirring with oxygen at a pressure of 20 kg/cm$^2$ for 2 hours. After this period about 89% of the combined ferrous and cobaltous ions are transformed to the higher oxidation state in the catalyst so prepared. The wt % of total ions, at this stage, of the catalyst prepared was found to be: cobaltic 79%, cobaltous 6%, ferric 13% and ferrous 2%.

EXAMPLE III

A solution of 16 g cobaltous adipate and 4 g ferrous adipate, 6 g paraldehyde, 150 g acetic acid was heated to 120° C. and treated with oxygen at a pressure of 10 kg/cm$^2$ for 4 hours. After this period 90% of the combined ferrous and cobaltous ions were transformed to the higher oxidation state. The composition of the catalyst prepared based on wt % of total ions was found to be: cobaltic 75%, cobaltous 5%, ferric 15% and ferrous 5%.

The catalyst so prepared in the above said examples can be used as such for oxidation of hydrocarbons like cyclohexane, cyclopentane, cycloheptane, toluene, C$_4$–C$_6$ paraffins, o-xylene, m-xylene, p-xylene for the preparation of corresponding dicarboxylic or monocarboxylic acids viz adipic acid, glutaric acid, pimelic acid, benzoic acid, acetic acid, isophthalic acid, phthalic acid, terephthalic acid and the like.

EXAMPLE IV 165 g of the resulting catalyst mixture from example I above and 35 g cyclohexane were reacted with oxygen at a space velocity of 25 h$^{-1}$ at 95° C., 20 kg/cm$^2$ in a 500 ml autoclave.

At the end of three hours, the reaction mixture was flashed to collect 80 g of the material containing 8.7 g of unreacted cyclohexane, 10.2 g water and 6.1 g of acetic acid. The residue on cooling to 25° C. yielded 24.0 g of crude 95% adipic acid crystals and 105 g filtrate plus acetic acid washings containing 9.6 g of adipic acid and 12.1 g partly oxidized products such as cyclohexanone, cyclohexanol, cyclohexyl acetate, monocyclohexyl adipate etc. and lower dicarboxylic acids which can be recycled. The cyclohexane conversion was 75.1% and the overall selectivity to adipic acid was 71%.

EXAMPLE V 35 g of cyclohexane, 165 g of the catalyst mixture from example II, was oxidised with oxygen at space velocity 20 h$^{-1}$ at 110° C., 30 Kg/cm$^2$. At the end of two hours, the reactor mixture was flashed to collect 100 g of a material containing 10.5 g of cyclohexane, 10.1 g water and 79.4 g acetic acid.

The residue on cooling and filtration yielded 25.3 g of crude 98.5% adipic acid. The filtrate contained 11.9 g adipic acid the cyclohexane conversion was 82% and overall selectivity to adipic acid was 73.8%.

EXAMPLE VI

A solution of 5.0 g cobaltous acetate tetrahydrate and 0.5 g of ferrous acetate 2 g cyclohexanone in 160 g glacial acetic acid was contacted at 95° C. with oxygen at a rage of 100 ml per minute with stirring for 2 hours when around 90% cobaltous as well as ferrous salts were converted to cobaltic and ferric salts. 35 g of cyclohexane was then added and the mixture further reacted with oxygen at a space velocity of 25 h$^{-1}$ at 95° C. and 49 Kg/cm$^2$ pressure. At the end of four hours the product was distilled to remove unreacted cyclohexane, water and some adipic acid. The residue was cooled and filtered to collect 23.8 g of 98.5% adipic acid. The filtrate contained 9.1 g adipic. The cyclohexane conversion recorded was 71% and overall selectivity to adipic was 76.8%.

EXAMPLE VII 175 g of the catalyst mixture from example III and 35 g Cyclohexane was treated for 6 hours at 100° C. at 30 Kg/cm$^2$ with oxygen at 50 ml per minute at the outlet. Overall selectivity to adipic acid was 74.5% and conversion of cyclohexane was 80%.

Though the present invention is described with Examples given above with particular reference to the preparation of adipic acid it should not be construed that the invention is restricted to the preparation of adipic acid only. The process of the present invention can be used for the preparation of dicarboxylic acids such as glutaric acid, pimellic acid, phthalic acid, isophthalic acid and terephthalic acid and monocarboxylic acids such as acetic acids, propionic acid and benzoic acid. This has been exemplified in the Examples given below.

EXAMPLE VIII

A solution of 40 g of p-xylene, 5.5 g of the catalyst containing 80% by weight cobaltic acetate, 10% ferric acetate, 8% cobaltous acetate and 2% ferrous acetate was reacted with oxygen at space velocity 30 h$^{-1}$ at 130° C., 10 Kg/cm$^2$ for four hours. The oxidate was flashed to collect 30.0 g of distillate containing, 4.0 g unreacted p-xylene, 8.2 g water and balance acetic acid. The residue was cooled and filtered, the solid was leached with acetic acid and dried to yield 51.9 g of crude 98% terephthalic acid corresponding to 90% p-xylene conversion and 92% isophthalic acid selectivity. The solution when recycled in fresh run yielded 53.5 g of terephthalic acid corresponding to 95% selectivity to terephthalic acid.

EXAMPLE IX

A solution of 40 g of m-xylene, 6 g of the catalyst containing (by weight) 85% cobaltic acetate, 8% ferric acetate 5% cobaltous acetate and 2% ferrous acetate and 200 g acetic acid was reacted with oxygen at space velocity 25 h$^{-1}$, at 135° C. and 20 Kg/cm$^2$ for four hours. The oxidate was flashed to collect 18.5 g distillate consisting of 3.5 g unreacted m-xylene, 8.5 g water and 6.5 g acetic acid. The residue, after cooling to room temperature, was filtered and the solid leached with acetic acid and dried to yield 53.4 g of 98% isophthalic acid, corresponding to 93.5% selectivity based on reacted m-xylene, which amounted to 91.2%. The filtrate when recycled in a fresh run resulted in 97% selectivity to isophthalic acid.

EXAMPLE X

A solution containing 30 g cyclopentane, 5.0 g catalyst consisting (by weight) 80% cobaltic acetate, 12% ferric acetate, 6% cobaltous acetate and 2% ferrous acetate and 150 g acetic acid was reacted with air at space velocity 60 h$^{-1}$ at 95° C. and 45 Kg/cm$^2$ for four hours. The oxidate was flashed to collect 50 g distillate consisting of 4 g unreacted cyclopentane, 0 g water and 36 g acetic acid. The residue contained 34.3 g glutaric acid corresponding to 86% cyclopentane conversion and 71% selectivity to glutaric acid.

EXAMPLE XI 200 g solution in acetic acid and containing 4.0 g catalyst consisting 85% cobaltic acetate 8% ferric acetate, 5% cobaltous acetate, and 2% ferrous acetic and 50 g toluene was reacted with oxygen at a space velocity of 40 h$^{-1}$ at 85° C. for four hours. The oxidation product on and work up yielded 61.7 g benzoic acid, 2.1 g benzaldehyde and 1.0 g unreacted toluene. This corresponded to 98% hydrocarbon conversion and 95% selectivity to benzoic acid and more than 40% benzaldehyde.

We claim:

1. A novel catalyst useful for the preparation of carboxylic acids by the oxidation of hydrocarbons which comprises 70–99% by weight of cobaltic salt and 1–30% by weight of ferric salt, the acid component of the salt being selected from the group consisting of acetate, propionate, naphthenate, adipate, and phthalate.

2. A novel catalyst as claimed in claim 1 wherein the catalyst contains 70–99% by wt. of cobaltic salt and 1–30% by wt. of ferric salt.

3. A process for the preparation of a new catalyst useful for the preparation of carboxylic acids by the oxidation of hydrocarbons which comprises reacting a mixture of 70–99% by weight of a cobaltous salt, 1–30% by weight of a ferrous salt, in the presence of an initiator, a solvent, selected from aliphatic mono-carboxylic acids having carbon atoms in the range of 2 to 4 or a mixture thereof and oxygen or air, at a temperature in the range of 60°–150° C. and pressure in the range of 1–50 Kg/cm$^2$ for a period in the range of 0.25–8 hours.

4. A process as claimed in claim 3 wherein the reaction is effected at a space velocity in the range of 10–90 h$^{-1}$.

5. A process as claimed in claim 4 wherein the amount of cobaltous salt ranges from 80–99% by weight, ferrous salt ranges from 1–20% by weight, initiator ranges from 10–100% by weight of the cobaltous salt, the solvent ranges from 2000–12000% by weight of the cobaltous salt, the space velocity ranges from 30–60 h$^{-1}$, the temperature ranges from 80°–150° C., the pressure ranges from 1–25 Kg/cm$^2$ and the period ranges from 0.5–3 hours.

6. A process as claimed in claim 3, wherein an initiator selected from the group consisting of 2-butanone, cyclohexanol, cyclohexanone, acetaldehyde, and partly oxidized hydrocarbons is used.

7. A process as claimed in claim 3, wherein a solvent selected from the group consisting of acetic, propionic, butanoic acid or their mixture is used.

8. A process for the preparation of carboxylic acid by oxidation of a hydrocarbon with oxygen or air which comprises:

(a) contacting the hydrocarbon with a catalyst comprising 70–99% by weight of cobaltic salt and 1–30% by weight of ferric salt, the acid component of the salt being selected from the group consisting of acetate, propionate, naphthenate, adipate and phthalate;

(b) contacting the resultant mixture with oxygen or air at a space velocity of 1–200 h$^{-1}$, temperature in the range of 60°–150° C., and pressure in the range of 1–70 Kg/cm$^2$ for a period in the range of 1–8 hours;

(c) separating the unreacted hydrocarbon and the catalyst by the conventional methods;

(d) separating the carboxylic acids formed by crystallization or by fractional distillation; and (e) recycling the recovered hydrocarbons, solvent and the catalyst in the steps (b) to (c) above.

9. A process as claimed in claim 8 wherein the catalyst to hydrocarbon ratio used ranges between 0.01 to 0.5 by weight; the pressure used ranges from 10–50 Kg/cm$^2$ and the temperature used ranges from 70°–150° C. and the space velocity ranges from 10–90 h$^{-1}$.

10. A process for the preparation of adipic acid by the oxidation of cyclohexane using a novel catalyst which comprises:

(a) contacting cyclohexane with a catalyst comprising a mixture of 70–99% by weight of a cobaltic salt, 1–30% by weight of a ferric salt, the acid component being selected from the group consisting of acetate, propionate, naphthenate adipate, and phthalate;

(b) contacting the resulting mixture with air or oxygen at a pressure in the range of 1–70 Kg/cm$^2$ and a temperature in the range of 70°–150° C. for a period in the range of 1–8 hours at a space velocity of 1–200 h$^{-1}$;

(c) separating the unreacted cyclohexane and the catalyst by conventional method;

(d) separating the adipic acid formed by crystallization or by fractional distillation; and (e) recycling the unreacted cyclohexane, the solvent and the catalyst from the steps (b) to (c).

\* \* \* \* \*

UNITED STATES PATENT AND TRADEMARK OFFICE
CERTIFICATE OF CORRECTION

PATENT NO.   : 5,547,905
DATED        : August 20, 1996
INVENTOR(S)  : KULSRESTHA ET AL.

It is certified that error appears in the above-identified patent and that said Letters Patent is hereby corrected as shown below:

On the title page, item [73] add assignee:

--Adarsh chemicals & Fertilizers LTD., Gujarat, India --.

Signed and Sealed this

Twelfth Day of December, 2000

Attest:

Q. TODD DICKINSON

*Attesting Officer*             *Director of Patents and Trademarks*